United States Patent [19]

Pauluth et al.

[11] Patent Number: 5,679,282
[45] Date of Patent: Oct. 21, 1997

[54] CHIRAL 2,6-DIFLUOROBENZENE DERIVATIVES

[75] Inventors: Detlef Pauluth, Ober-Ramstadt; Herbert Plach, Darmstadt, both of Germany

[73] Assignee: Merck Patent Gesellschaft mit beschrankter Haftung, Darmstadt, Germany

[21] Appl. No.: 462,708

[22] Filed: Jun. 5, 1995

Related U.S. Application Data

[62] Division of Ser. No. 384,463, Feb. 2, 1995, which is a continuation of Ser. No. 95,461, Jul. 23, 1993, abandoned.

[30] Foreign Application Priority Data

Jul. 24, 1992 [DE] Germany .................. 42 24 460.9

[51] Int. Cl.$^6$ .................. C09K 19/52; C09K 19/34; C09K 19/30; C09K 19/12
[52] U.S. Cl. .................. 252/299.01; 252/299.61; 252/299.63; 252/299.65; 252/299.66; 252/299.67
[58] Field of Search .................. 252/299.63, 299.66, 252/299.01, 299.61

[56] References Cited

U.S. PATENT DOCUMENTS

| | | | |
|---|---|---|---|
| 4,551,264 | 11/1985 | Eidenschink et al. | 252/299.62 |
| 4,963,288 | 10/1990 | Saito et al. | 252/299.61 |
| 5,120,468 | 6/1992 | Saito et al. | 252/299.61 |
| 5,230,829 | 7/1993 | Bartmann et al. | 252/299.63 |
| 5,273,680 | 12/1993 | Gray et al. | 252/299.66 |
| 5,275,756 | 1/1994 | Yamaguchi et al. | 252/299.61 |
| 5,281,362 | 1/1994 | Nohira et al. | 252/299.61 |
| 5,290,478 | 3/1994 | Satoh et al. | 252/299.62 |
| 5,298,188 | 3/1994 | Vergnolle et al. | 252/299.63 |
| 5,300,254 | 4/1994 | Geelhaar et al. | 252/299.61 |
| 5,318,721 | 6/1994 | Reiffenrath et al. | 252/299.63 |
| 5,324,449 | 6/1994 | Kurmeier et al. | 252/299.01 |

FOREIGN PATENT DOCUMENTS 2-157248  6/1990  Japan.

OTHER PUBLICATIONS

Weber et al., Liquid Crystals, vol. 5, No. 5, pp. 1381–1388 (1989).

*Primary Examiner*—C. H. Kelly
*Attorney, Agent, or Firm*—Millen, White, Zelano & Branigan, P.C.

[57] ABSTRACT

The invention relates to chiral 2,6-difluorobenzene derivatives of the formula I

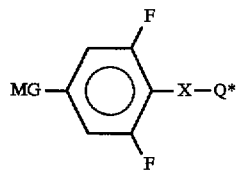

in which
MG is a mesogenic group containing no ester groups, or a group which in combination with

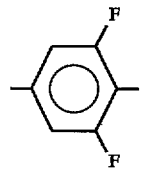

forms a mesogenic group containing no ester groups;
X is O or $CH_2$; and
$Q^*$ is a chiral radical containing at least one chiral carbon atom,
and to the use thereof as chiral dopes in liquid-crystalline media for electrooptical displays.

46 Claims, No Drawings

CHIRAL 2,6-DIFLUOROBENZENE DERIVATIVES

This is a division of application Ser. No. 08/384,463 filed Feb. 2, 1995, which is a continuation of Ser. No. 08/095,461, filed Jul. 23, 1993 now abandoned.

The invention relates to chiral 2,6-difluorobenzene derivatives of the formula I

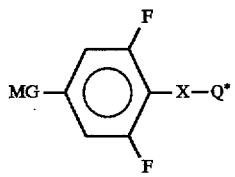

in which

MG is a mesogenic group containing no ester groups or a group which, in combination with

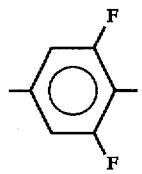

forms a mesogenic group containing no ester groups,

X is O or $CH_2$, and

Q* is a chiral radical containing at least one chiral carbon atom.

In particular in the last decade, liquid crystals have been introduced into various industrial areas in which electro-optical and display device properties are required (for example in watch, calculator and typewriter displays). These display devices are based on dielectric alignment effects in the nematic, cholesteric and/or smectic phases of the liquid-crystalline compounds, the molecular long axis of the compounds adopting a preferential alignment—caused by the dielectric anisotropy—in an applied electrical field. The usual response times in these display devices are too long for many other potential areas of application of liquid crystals. This disadvantage is particularly noticeable if a large number of pixels have to be addressed. The production costs of equipment containing relatively large screen areas, such as, for example, of video equipment, are then generally too high.

In addition to nematic and cholesteric liquid crystals, optically active smectic liquid-crystal phases have also increased in importance in the last few years.

Clark and Lagerwall were able to show that the use of ferroelectric liquid-crystal systems in very thin cells gives opto-electrical switching or display elements which have response times a factor of up to 1000 faster than conventional TN ("twisted nematic") cells (cf., for example, Lagerwall et al., "Ferroelectric Liquid Crystals for Displays", SID Symposium, October Meeting 1985, San Diego, Calif., U.S.A.). Due to these and other favorable properties, for example the possibility of bistable switching and the virtually viewing angle-independent contrast, FLCs are in principle highly suitable for the abovementioned areas of application, for example via matrix addressing.

For electro-optical switching and display elements, there is either a need for compounds which form tilted or orthogonal smectic phases and are themselves optically active, or ferroelectric smectic phases can be induced by doping compounds which, although forming smectic phases of this type, are not themselves optically active with optically active compounds. The desired phase should be stable over the broadest possible temperature range.

In order to achieve good contrast in electro-optical components, a uniform planar alignment of the liquid crystals is necessary. Good alignment in the $S^*_A$ and $S^*_C$ phases can be achieved if the phase sequence in the liquid-crystal mixture is as follows, with decreasing temperature:

$$\text{Isotrope} \rightarrow N^* \rightarrow S^*_A \rightarrow S^*_C$$

The prerequisite is that the pitch of the helix in the N* phase is very large (greater than 10 μm) or, still better, is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid., p. 344–p. 347). This is achieved by adding a further optically active dope which induces a right-hand helix to the chiral liquid-crystal mixture which has, for example, a left-hand helix in the N* phase in such a manner that the helix is just compensated.

It has now been found that optically active 2,6-difluorobenzene derivatives of the formula I cause, as dopes in tilted smectic liquid-crystal phases, a high degree of twist in the cholesteric phase even when added in small amounts.

This helix induced in the N* phase can advantageously be used in mixtures for specific compensation of the pitch. It is particularly advantageous that the dopes according to the invention, due to their high twist capacity, compensate the pitch of another dope even when added in small amounts.

JP-A 2 157 248 discloses similar, optically active 2,6-difluorobenzene derivatives. However, these contain an ester group and are not suitable for helix compensation, since they have a large pitch themselves. In addition, these compounds have a voltage holding ratio which is insufficient for active matrix addressing (for example G. Weber et al., Liquid Crystals 5, 1381 (1989)).

The invention therefore relates to the chiral 2,6-difluorobenzene derivatives of the formula I, particularly in which MG is a radical of the formula II $$R^1 \text{—} (A^1 \text{—} Z^1)_1 \text{—} A^2 \text{—} Z^2 \quad\quad\quad II$$

in which $R^1$ is F, Cl, $CF_3$, $OCF_3$, $OCF_2H$, CN or an alkyl or alkenyl radical, in each case having 1 to 18 carbon atoms, which is unsubstituted or at least monosubstituted by halogen or monosubstituted by cyano and in which, in addition, one or two non-adjacent $CH_2$ groups may be replaced by —O— or —S—, $A^1$ and $A^2$ are each, independently of one another, 1,4-phenylene which is unsubstituted or substituted by 1 or 2 fluorine atoms and in which, in addition, one or two CH groups may be replaced by N, or are 1,4-cyclohexylene which is unsubstituted or substituted by one cyano group and in which, in addition, one or two $CH_2$ groups may be replaced by O or S, or are thiadiazole-2,5-diyl or 1,4-bicyclo[2.2.2]octylene, $Z^1$ and $Z^2$ are each —$OCH_2$—, —$CH_2O$—, —$CH_2CH_2$—, —C≡C— or a single bond, and is 0, 1, 2 or 3.

Preferred embodiments are:

a) chiral derivatives in which Q* is a radical of the formula III

 III in which
Q¹ and Q² are each a $C_{1-8}$-alkylene group in which, in addition, one or two $CH_2$ groups may be replaced by —O— or —S— in such a way that two hetero atoms are not adjacent,
R⁰ is H or a $C_{1-6}$-alkyl group which is different from Y,
Y is $CH_3$, halogen, $CF_3$, $CF_2H$, $CH_2F$ or CN,
R² is $C_{1-6}$-alkyl, and
C* is a chiral carbon atom having four different substituents,
where the groups R⁰, Y and —Q²—R² are in each case different from one another;

b) chiral derivatives in which Q* is a radical of the formula IV

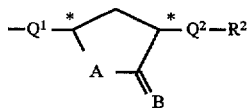 IV in which
Q¹, Q² and R² are as defined in Formula III, and
A is O, S or NH, and
B is $H_2$, $CH_2$, O or S;

c) chiral derivatives in which Q* is a radical of the formula V

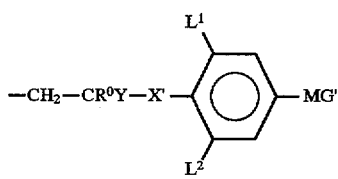 V in which
R⁰ and Y are as defined in Formula III, and
X' is —O—, —$CH_2$— or a single bond,
MG' is a mesogenic group containing no ester groups or is a group which in combination with

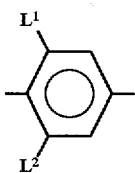

forms a mesogenic group containing no ester groups;
L¹ and L² are each H or F;

d) chiral derivatives of the formula I1

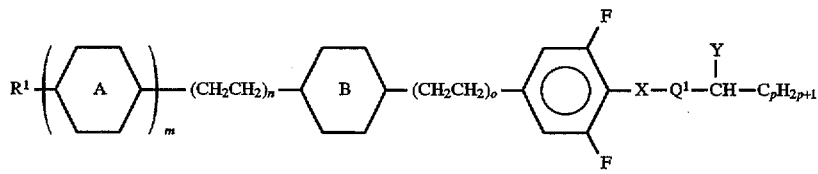 I1 in which
R¹, X, Q¹ and Y are as defined above, and

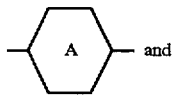 and

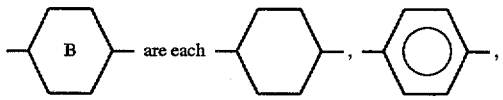

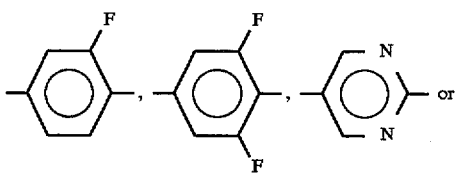 or

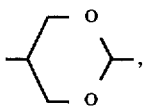, m 0, 1 or 2,
n and o are each 0 or 1, and
p is from 2 to 8.

The invention furthermore relates to liquid-crystalline media containing at least two liquid-crystalline components, characterized in that they contain at least one ester group-free compound which contains a structural element of the formula VI

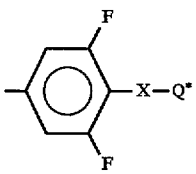 VI in which X and Q* are as defined above, in particular liquid-crystalline media which contain a derivative of the formula I.

The invention furthermore relates to electrooptical displays containing a liquid-crystalline medium of this type, in particular a supertwist liquid-crystal display having
two plane-parallel outer plates which, together with a frame, form a cell,
a nematic liquid-crystal mixture of positive dielectric anisotropy in the cell,
electrode layers covered by alignment layers on the insides of the outer plates,
a pitch angle between the long axes of the molecules at the surface of the outer plates and the outer plates of preferably about 1 degree–30 degrees, and
a twist angle of the liquid-crystal mixture in the cell from alignment layer to alignment layer having a value of preferably about 100°–600°, where the nematic liquid-crystal mixture
a) is based on component A, comprising one or more compounds having a dielectric anisotropy of +1.5–+40,
b) contains about 0–40% by weight of a liquid-crystalline component B, comprising one or more compounds having a dielectric anisotropy of about −1.5–+1.5,
c) contains about 0–20% by weight of a liquid-crystalline component C, comprising one or more compounds having a dielectric anisotropy of less than about −1.5, and
d) contains an optically active component D in such an amount that the ratio between the cell thickness (distance between the plane-parallel outer plates) and the natural pitch of the chiral nematic liquid-crystal mixture (p) is about 0.025–1.0, the optically active component D contains at least one compound of the formula I, and the nematic liquid-crystal mixture has a nematic phase range of at least about 60° C., a viscosity of not more than about 35 mPa.s and a dielectric anisotropy of at least about +1, where the dielectric anisotropy of the compounds and the parameters based on the nematic liquid-crystal mixture are measured at a temperature of 20° C.

The amount of component A is preferably about 40–90%, especially 55–85%, based on the total liquid crystal mixture. The amount of component B is preferably about 10–40%, especially 15–25%, and the amount of component C is preferably about 2–20%, especially 5–15%, based on the total liquid-crystal mixture.

The invention also relates to chiral tilted smectic liquid-crystalline media containing at least one compound of the formula I, in particular to a ferroelectric liquid-crystalline medium containing an achiral smectic component S which contains at least one achiral smectic liquid-crystalline compound, and a chiral component D containing at least one chiral dope, wherein the chiral dope is a compound of the formula I.

Based on the total liquid-crystal mixture, the amount of component S is preferably about 80–98%, especially 85–95%, and the amount of component D is preferably about 2–20%, especially 5–15%.

The invention furthermore relates to electrooptical display elements which contain phases of this type, in particular a liquid-crystal, switching and display device of this type containing a ferroelectric liquid-crystalline medium, outer plates, electrodes, at least one alignment layer and, if desired, additional auxiliary layers, where the ferroelectric medium containing at least one compound of the formula I is a medium containing at least two liquid-crystalline components, wherein said medium contains at least one compound having a structural element of formula VI,

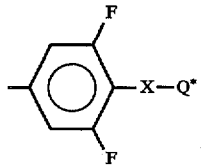

VI in which X is O or CH$_2$, and Q* is a chiral radical containing at least one chiral carbon atom.

The invention furthermore relates to electrooptical display elements having active matrix addressing, which contain nematic or cholesteric phases containing at least one compound of the formula I.

The term mesogenic group is known to persons skilled in the art (for example, H. Kelker, H. Hatz, Handbook of Liquid Crystals) and, in the context of the invention, denotes a rod-like radical comprising ring members, optionally bridging members and wing groups.

The term "ester group-free" means that the mesogenic group contains no carboxylate groups —O—CO— and/or —CO—O—.

Above and below, MG, MG', A, B, R$^1$, R$^2$, R$^0$, A$^1$, A$^2$, Q*, Q$^1$, Q$^2$, Y, X, X', L$^1$, L$^2$, Z$^1$, Z$^2$, l, m, n, o and p have the stated meaning, unless expressly stated otherwise.

Above and below, PhFF denotes a 2,6-difluoro-1,4-phenylene group of the formula

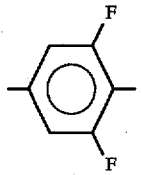

The compounds of the formula I accordingly include, in particular, compounds of the sub-formulae Ia to Ih:

| | |
|---|---|
| R$^1$—A$^2$—PhFF—Q* | Ia |
| R$^1$—A$^2$—Z$^2$—PhFF—Q* | Ib |
| R$^1$—A$^1$—A$^2$—PhFF—Q* | Ic |
| R$^1$—A$^1$—A$^2$—Z$^2$—PhFF—Q* | Id |
| R$^1$—A$^1$—Z$^1$—A$^2$—PhFF—Q* | Ie |
| R$^1$—A$^1$—Z$^1$—A$^2$—Z$^2$—PhFF—Q* | If |
| R$^1$—A$^1$—A$^1$—A$^2$—PhFF—Q* | Ig |
| R$^1$—A$^1$—A$^1$—Z$^1$—A$^2$—PhFF—Q* | Ih |

Of these, those of the formulae Ia, Ib, Ic, Id and Ie are particularly preferred.

Compounds of the formulae above and below containing branched wing groups R$^1$ may be of importance. Branched groups of this type generally contain not more than two chain branches. R$^1$ is preferably a straight-chain group or a branched group containing not more than one chain branch.

Preferred branched radicals are isopropyl, 2-butyl (=1-methylpropyl), isobutyl (=2-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylpentoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

The radical R$^1$ and in particular also the radical R$^2$ may alternatively be an optically active organic radical containing an asymmetrical carbon atom.

R$^1$ and R$^2$ are preferably alkyl or alkenyl having up to 15 carbon atoms. Particular preference is given to alkyl having 5 to 12 carbon atoms, i.e., pentyl, hexyl, heptyl, octyl, nonyl, decyl, undecyl and dodecyl. These groups may be straight-chain or branched, straight-chain alkyl groups being preferred. However, R$^2$ is also preferably methyl or branched alkyl containing a methyl branch, for example isopropyl.

Z$^1$ and Z$^2$ are preferably each, independently of one another, —CH$_2$CH$_2$—, —C≡C— or a single bond, particularly preferably a single bond.

l is preferably 0 or 1, o is preferably 0 or 1, and n is preferably 0.

The radicals A$^1$ and A$^2$ preferably have one of the meanings 1–8 below:

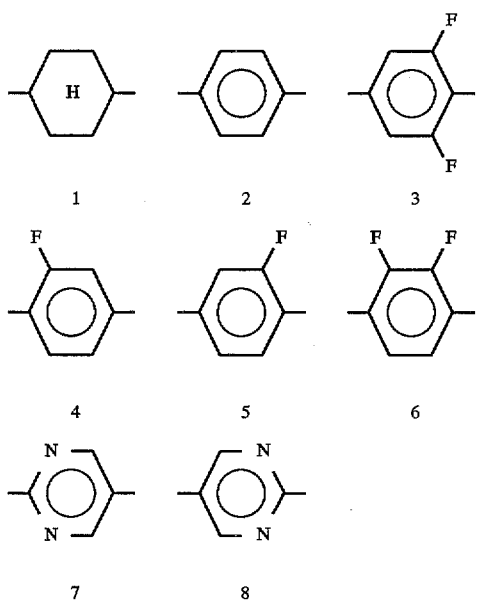

Meanings 2, 4, 5 and 6, in particular 6, are particularly preferred.

Of these compounds of the formula I and of the sub-formulae, those are preferred in which at least one of the radicals present therein has one of the preferred meanings indicated.

Some very particularly preferred smaller groups of compounds are those of the sub-formulae Ia1 to Ie3:

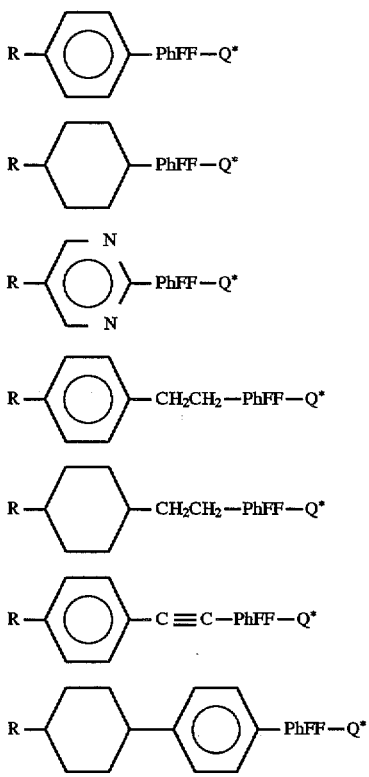

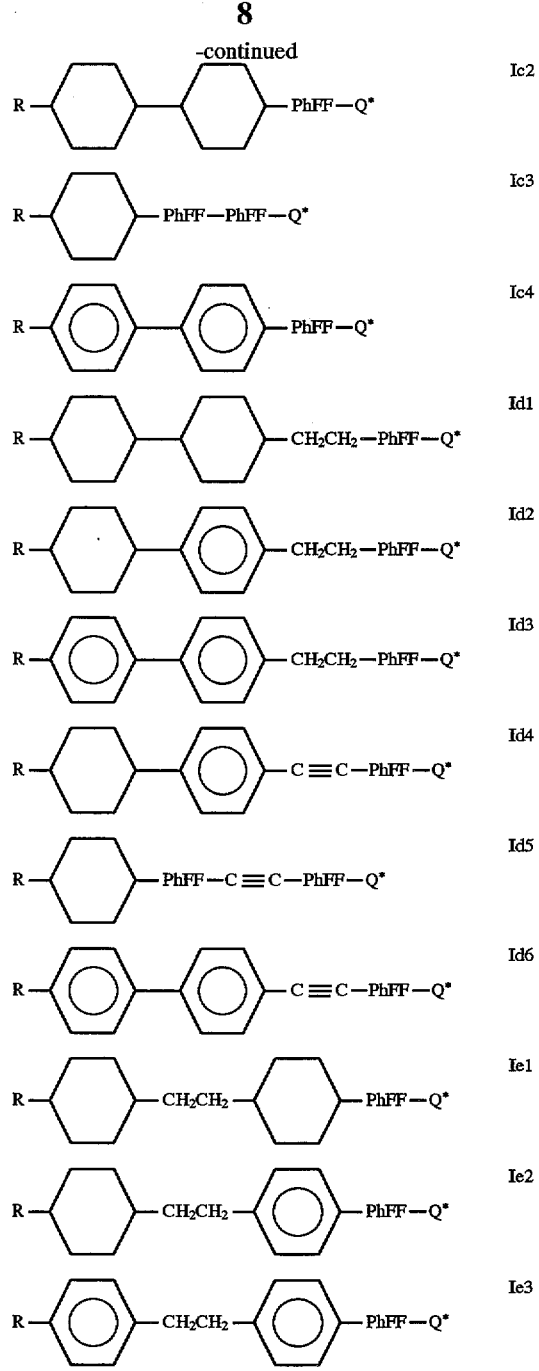

Preferred chiral radicals of the formula III are those of the formulae IIIa to IIIf:

| | |
|---|---|
| —(CH$_2$)$_m$—CH(CH$_3$)—C$_n$H$_{2n+1}$ | IIIa |
| —O—(CH$_2$)$_m$—CH(CH$_3$)—C$_n$H$_{2n+1}$ | IIIb |
| —(CH$_2$)$_m$—CHF—C$_n$H$_{2n+1}$ | IIIc |
| —O—(CH$_2$)$_m$—CHF—C$_n$H$_{2n+1}$ | IIId |
| —(CH$_2$)$_m$—CH(CN)—C$_n$H$_{2n+1}$ | IIIe |
| —O—(CH$_2$)$_m$—CH(CN)—C$_n$H$_{2n+1}$ | IIIf | in which in each case
m is 0 to 8, preferably 0 to 2, and
n is 2 to 14, preferably 2 to 10.
Preferred chiral radicals of the formula IV are those of the formulae IVa and IVb:

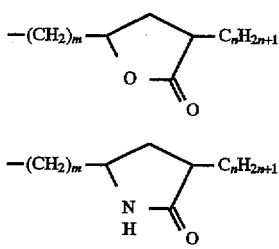
IVa

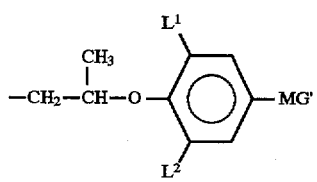
IVb in which in each case m is 0 to 8, preferably 1, and n is 2 to 14, preferably 2 to 10.

Preferred radicals of the formula V are those of the formula Va:

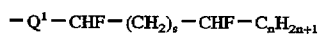
Va

Further preferred meanings of Q* are the radicals of the formulae VI and VII:

$-Q^1-CHF-(CH_2)_s-CHF-C_nH_{2n+1}$   VI

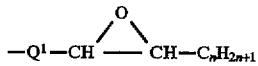
VII in which s is 0 to 6, and n is 1 to 10.

The compounds of the formula I are prepared by methods known per se, as described in the literature (for example, in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not described in greater detail.

The compounds of the formula I in which Q* is a radical of the formula III and X is O are prepared in accordance with Scheme 1:

Scheme 1

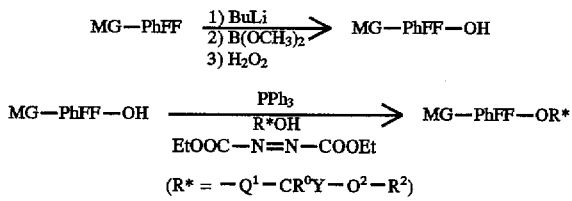

$(R^* = -Q^1-CR^0Y-O^2-R^2)$

The compounds of the formula I in which Q* is a radical of the formula III and X is a single bond are prepared in accordance with Scheme 2:

Scheme 2

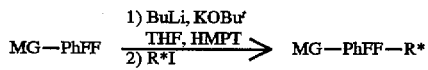

The compounds of the formula I in which Q* is a radical of the formula IV are prepared in accordance with Scheme 3:

Scheme 3

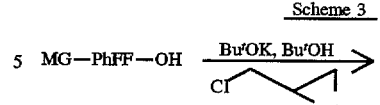

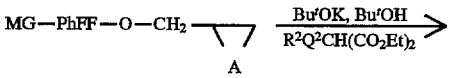

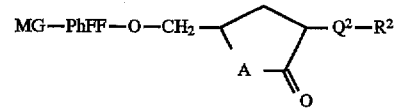

The compounds of the formula I in which Q* is a radical of the formula V are prepared in accordance with Scheme 4:

Scheme 4

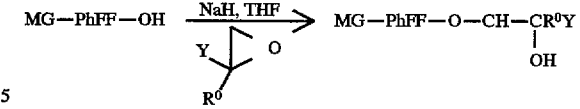

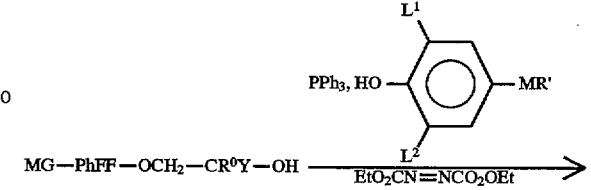

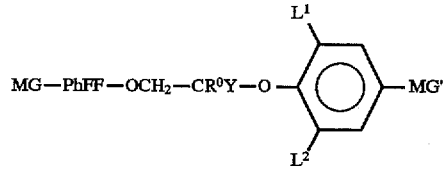

The media according to the invention contain at least one, preferably at least two, compounds of the formula I. The ferroelectric media according to the invention preferably contain an achiral smectic component S containing at least one achiral smectic compound, and a chiral component D which contains at least one chiral dope, where at least one chiral compound is a compound of the formula I. Particular preference is given to chiral tilted smectic liquid-crystalline phases according to the invention whose achiral base mixture contains, in addition to compounds of the formula I, at least one other component having negative or low positive dielectric anisotropy. The chirality is preferably based partially or fully on chiral compounds of the formula I. These phases preferably contain one or two chiral compounds of the formula I. However, it is also possible to employ achiral compounds of the formula I (for example in the form of a racemate), in which case the chirality of the phase is caused by other optically active compounds. If chiral compounds of the formula I are used, mixtures having an enantiomer excess are also suitable in addition to the pure optical antipodes. The abovementioned other component(s) of the achiral base mixture can make up from 1 to 50%, preferably from 10 to 25%, of the base mixture.

The compounds of the formula I are also suitable as components of nematic liquid-crystalline phases, for example for preventing reverse twist.

Furthermore, the compounds of the formula I can be employed as dopes for nematic liquid-crystalline phases for STN and active matrix displays. In this case, they are distinguished, in particular, by a high helical twisting power (HTP) and by a high voltage holding ratio. In particular, doped, nematic mixtures of this type can easily be purified by treatment with aluminum oxide, with no or virtually no loss of chiral dope occurring.

In addition, chiral 2,6-difluorobenzene derivatives according to the invention can be used to prepare liquid-crystalline media for so-called phase change displays (for example Y. Yabe et al., SID 1991 Digest, 261–264).

These liquid-crystalline media according to the invention comprise 2 to 25, preferably 3 to 15 components, including at least one compound of the formula I. The other constituents are preferably selected from smectic or smectogenic substances, in particular known substances, from the classes comprising the azoxybenzenes, benzylidene anilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexylpyridazines and their N oxides, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids. The smectic component S is based on the achiral compounds of this type.

The most important compounds which are suitable as components of liquid-crystalline phases of this type can be characterized by the formula I'

R'—L—G—E—R"  I' in which L and E are each a carbocyclic or heterocyclic ring system from the group consisting of 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or a C—C single bond,

Y is halogen, preferably chlorine, or —CN, and R' and R" are alkyl, alkoxy, alkanoyloxy, alkoxycarbonyl or alkoxycarbonyloxy having 1 to 8, preferably 5 to 12, carbon atoms, or one of these radicals is alternatively F, —CF$_3$—, —OCF$_3$ or CN.

In most of these compounds, R' and R" are each alkyl or alkoxy groups of different chain length, where the total number of carbon atoms is generally greater than 12, preferably from 12 to 20, in particular from 13 to 18. However, other variants of the proposed substituents are also common. Many such substances or mixtures thereof are commercially available. All these substances can be prepared by methods which are known from the literature.

The media according to the invention contain about 0.1 to 99%, preferably 10 to 95%, of one or more compounds of the formula I. Additionally preferred are liquid-crystalline phases according to the invention which contain 0.1–40%, preferably 0.5–10%, of one or more compounds of the formula I.

Further mixture components of component S are preferably compounds of the formulae below.

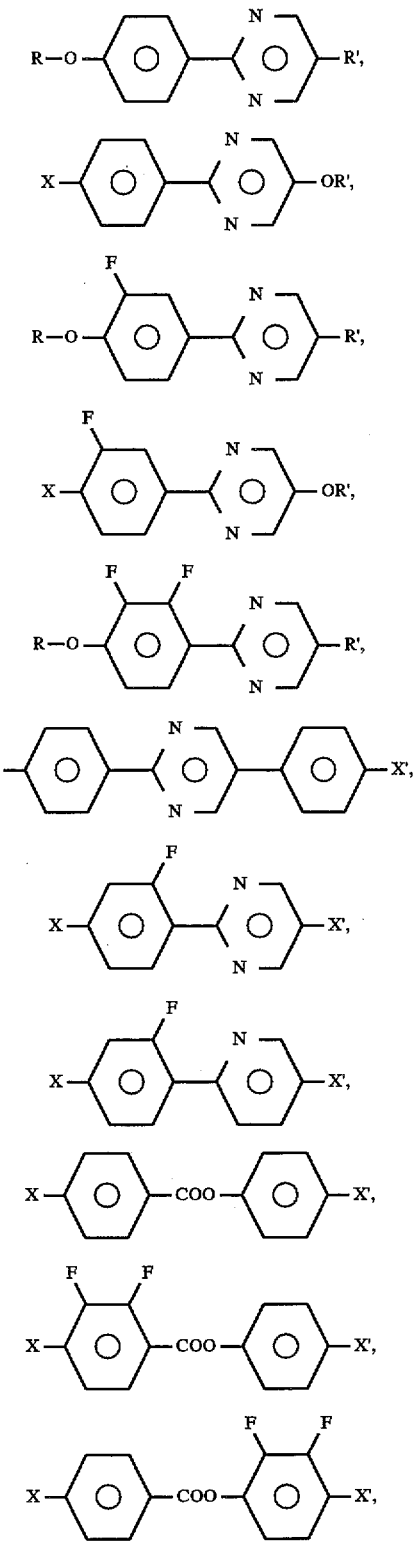

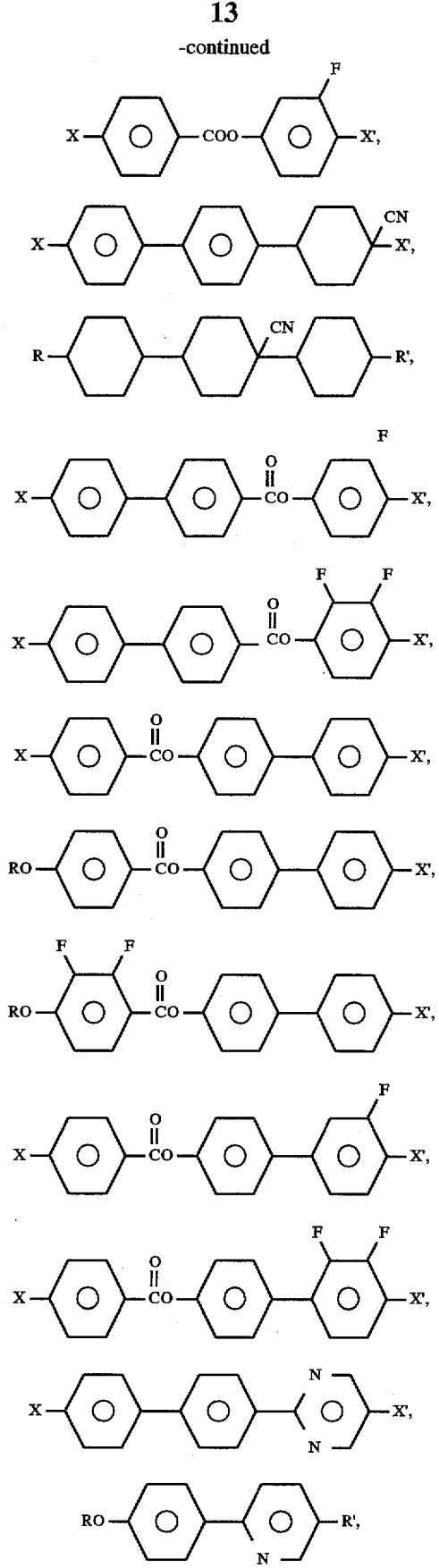
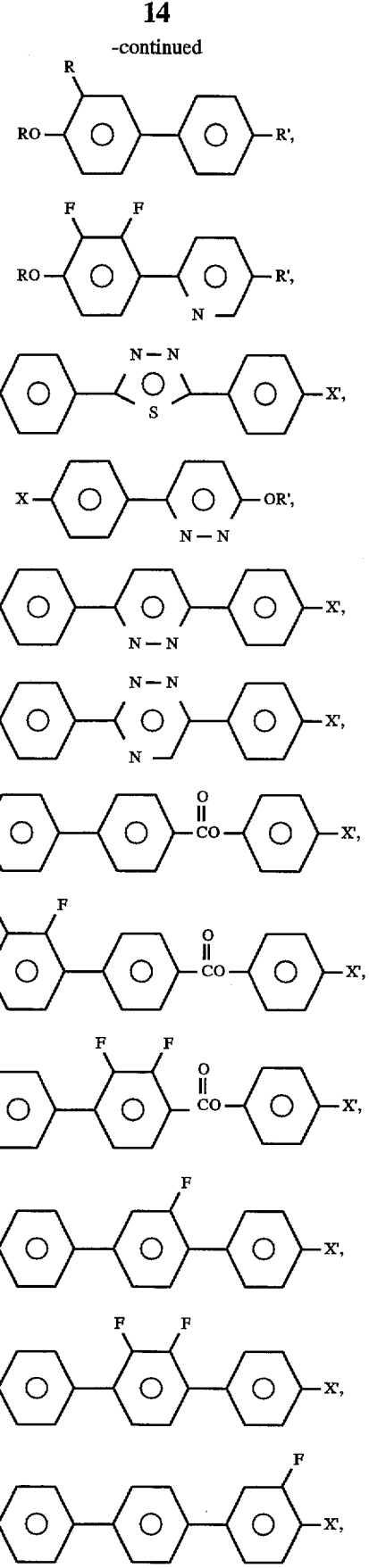

-continued

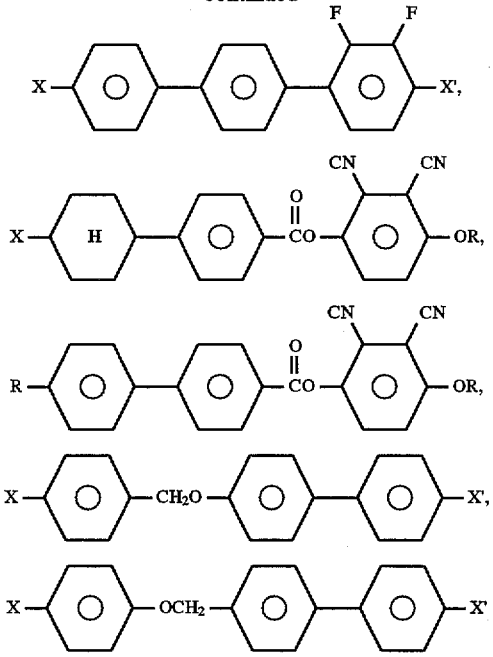

in which R and R' are each, independently of one another, alkyl having 5 to 18 carbon atoms and X and X' are each, independently of one another, alkyl, alkoxy, polyfluoroalkyl or polyfluoroalkoxy having 5 to 18 carbon atoms.

The phases according to the invention are prepared in a manner known per se. In general, the components are dissolved in one another, expediently at elevated temperature.

By means of suitable additives, the liquid-crystalline phases of the invention can be modified so that they can be used in all types of liquid-crystal display elements which have been disclosed hitherto, in particular of the SSFLC type (Surface Stabilized Ferroelectric Liquid Crystal) in the chevron or bookshelf geometry. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 42 24 460.9, filed Jul. 24, 1992, are hereby incorporated by reference.

EXAMPLES

The examples below are intended to illustrate the invention without representing a limitation. M.p.=melting point, c.p.=clearing point. Above and below, percentages are by weight; all temperatures are given in degrees Celsius. "Customary "work-up" means that water is added, the mixture is extracted with dichloromethane, the organic phase is separated off, dried and evaporated, and the product is purified by crystallization and/or chromatography.

In the present application and in the Examples below, the structures of the liquid-crystal compounds are indicated by acronyms, the transformation in chemical formulae being carried out in accordance with Tables A and B below. All radicals $C_nH_{2n+1}$ and $C_mH_{2m+1}$ are straight-chain alkyl radicals having n and m carbon atoms, respectively. The coding in Table B is self-explanatory. In Table A, only the acronym for the parent structure is given. In individual cases, the acronym for the parent structure is followed, separated by a hyphen, by a code for the substituents $R^1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | F | H |
| nOmFF | $C_nH_{2n+1}$ | $OC_mH_{2m+1}$ | F | F | H |
| nmF | $C_nH_{2n+1}$ | $C_mH_{2m+1}$ | F | H | H |
| $nCF_3$ | $C_nH_{2n+1}$ | $CF_3$ | H | H | H |
| $nOCF_3$ | $C_nH_{2n+1}$ | $OCF_3$ | H | H | H |
| $nOCF_2$ | $C_nH_{2n+1}$ | $OCHF_2$ | H | H | H |
| nS | $C_nH_{2n+1}$ | NCS | H | H | H |
| rVsN | $C_rH_{2r+1}$—CH=CH—$C_sH_{2s}$— | CN | H | H | H |
| rEsN | $C_rH_{2r+1}$—O—$C_sH_{2s}$— | CN | H | H | H |
| nNF | $C_nH_{2n+1}$ | CN | F | H | H |
| nAm | $C_nH_{2n+1}$ | $COOC_mH_{2m+1}$ | H | H | H |
| nF.F.F | $C_nH_{2n+1}$ | F | H | F | F |
| $nOCF_3$.F | $C_nH_{2n+1}$ | $OCF_3$ | H | F | H |
| $nOCF_3$.F.F | $C_nH_{2n+1}$ | $OCF_3$ | H | F | F |
| nCl.F | $C_nH_{2n+1}$ | Cl | H | F | H |
| nCl.F.F | $C_nH_{2n+1}$ | Cl | H | F | F |

TABLE A
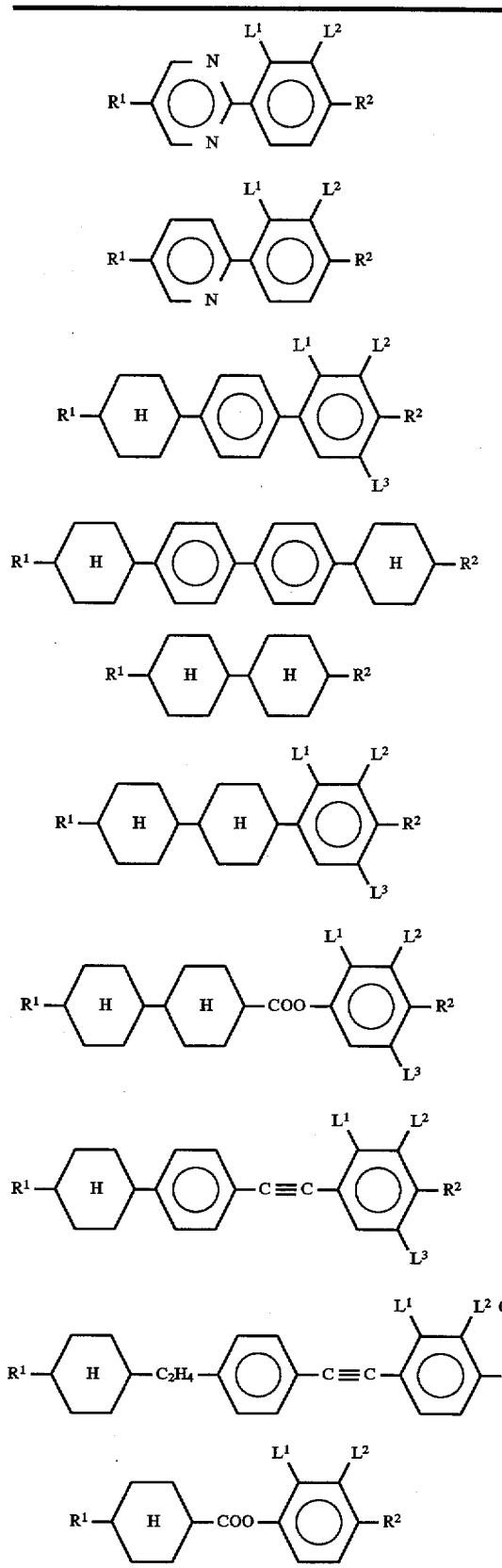
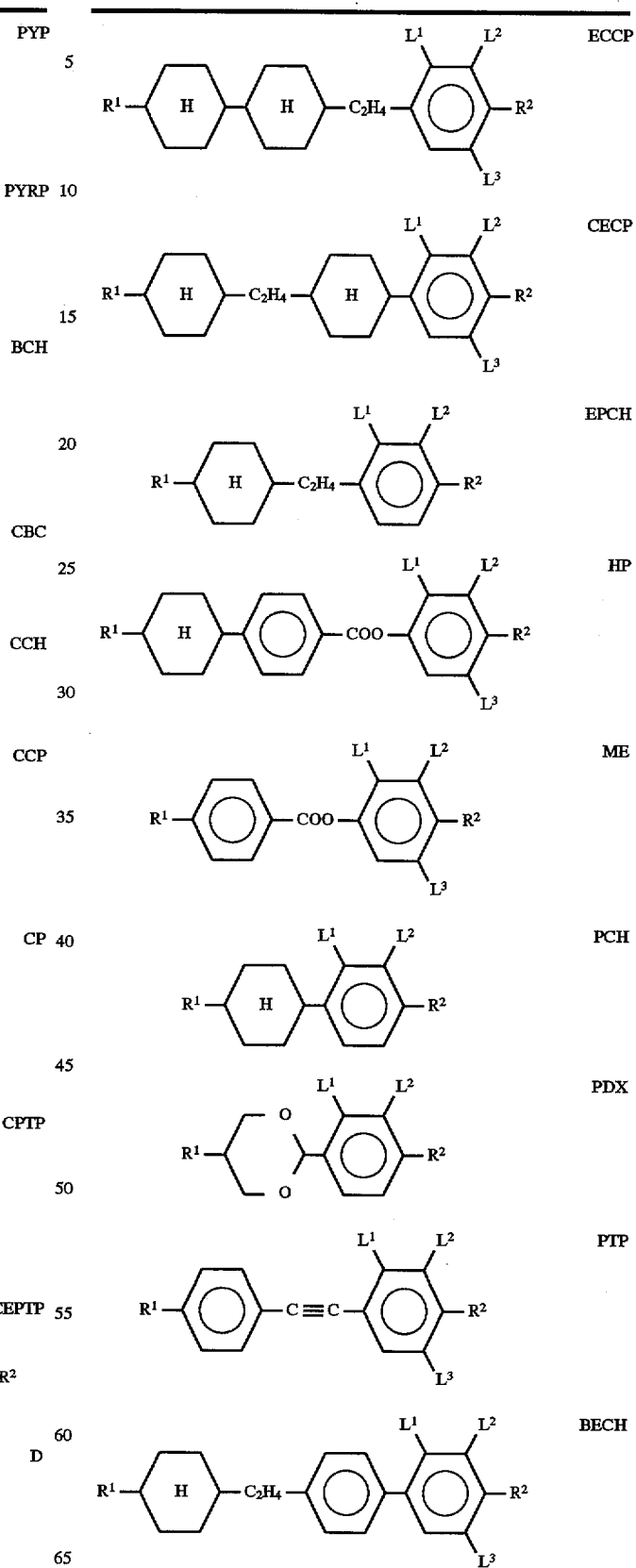

TABLE A-continued
TABLE B
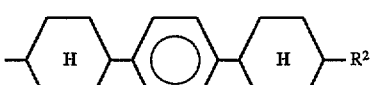
TABLE B-continued
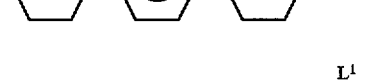

TABLE B-continued

| Structure | Name |
|---|---|
| C_nH_{2n+1}—[H]—[◯(F,F,F)] | BCH-nF.F.F |
| C_nH_{2n+1}—[H]—[◯(F,F)]—[◯]—F | CUP-nF |
| C_nH_{2n+1}—[H]—[◯(F,F)]—[◯]—Cl | CUP-nCl |
| C_nH_{2n+1}—[H]—C_2H_4—[◯(F,F)]—[◯]—F | CEUP-nF |
| C_nH_{2n+1}—[H]—[◯(F,F)]—[◯(F,F)]—F | C UP-nF.F |
| C_nH_{2n+1}—[H]—[H]—[◯(F,F)]—OCF_2H | CCP-nOCF2.F.F |
| C_nH_{2n+1}—[H]—[◯(CN)]—[H]—C_mH_{2m+1} | BCN-nm |

In addition, the following abbreviations are used: C: crystalline-solid state, S: smectic phase (the index denotes the phase type), N: nematic state, Ch: cholesteric phase, I: isotropic phase. The number between two symbols indicates the conversion temperature in degrees Celsius.

Example 1

2.6 ml (16 mmol) of diethyl azodicarboxylate are added dropwise at room temperature to a mixture of 5 g (15 mmol) of 4-[trans-4-(trans-4-propylcyclohexyl)cyclohexyl]-2,6-difluorophenol, 2.1 g (16 mmol) of (S)-(+)-2-octanol, 4.3 g of triphenylphosphine and 80 ml of THF. The mixture is stirred for 2 hours and subjected to customary work-up. Chromatography gives (R)-(−)-4-[trans-4-(trans-4-propylcyclohexyl)cyclohexyl]-1-(1-methylheptyloxy)-2,6-difluorobenzene, C 29 S_B 42 Ch 73.8 I, HTP=−7.7, $[\alpha]_D^{20}$= −6.9 (CH_2Cl_2).

The following are prepared analogously:

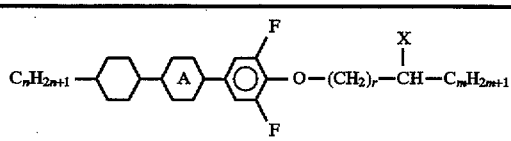

| n | A | r | X | m | |
|---|---|---|---|---|---|
| 3 | —◯— (cyclohexyl) | 0 | CH_3 | 3 | C 99 Ch 130.5 I, $[\alpha]_D^{20}$=+3.0 (CH_2Cl_2) |
| 5 | —◯— | 0 | CH_3 | 7 | |
| 7 | —◯— | 0 | CH_3 | 7 | |
| 8 | —◯— | 0 | CH_3 | 7 | |
| 3 | —◯— (phenyl) | 0 | CH_3 | 7 | |
| 5 | —◯— | 0 | CH_3 | 7 | |
| 7 | —◯— | 0 | CH_3 | 7 | |
| 8 | —◯— | 0 | CH_3 | 7 | |
| 3 | —◯— (cyclohexyl) | 1 | F | 6 | C 45 S_B 83 S_A 86 Ch 127.8 I, $[\alpha]_D^{20}$+3,4 (CH_2Cl_2) |
| 5 | —◯— | 1 | F | 6 | |
| 7 | —◯— | 1 | F | 6 | |
| 9 | —◯— | 1 | F | 6 | |
| 3 | —◯— (phenyl) | 1 | F | 6 | |
| 5 | —◯— | 1 | F | 8 | |
| 7 | —◯— | 1 | F | 8 | |
| 9 | —◯— | 2 | F | 6 | |

Example 2

51 mmol of a solution of n-BuLi in hexane are added dropwise at −100° C. to a mixture of 46 mmol of 4-(trans-4-propylcyclohexyl)-2,6-difluorobenzene, 500 ml of THF and 51 mmol of potassium tert-butoxide. After the mixture has been stirred for 1 hour, a solution of 60 mmol of (S)-(+)-2-methylbutyl iodide, 6 g of N-dimethylpropyleneurea and 15 ml of THF is added dropwise. The reaction mixture is stirred at from −90° C. to −70° C. for one hour and warmed to −10° C. Customary work-up and chromatography give: 4-(trans-4-propylcyclohexyl)-2,6-difluoro-1-(2-methylbutyl)benzene.

The following are prepared analogously:

$C_nH_{2n+1}$—A—[2,6-difluorophenyl]—O—$(CH_2)_r$—CH(X)—$C_mH_{2m+1}$

| n | A | r | X | m |
|---|---|---|---|---|
| 5 | cyclohexyl | 1 | CH$_3$ | 2 |
| 7 | cyclohexyl | 1 | CH$_3$ | 2 |
| 3 | phenyl | 1 | CH$_3$ | 2 |
| 5 | phenyl | 1 | CH$_3$ | 2 |
| 7 | phenyl | 1 | CH$_3$ | 2 |
| 3 | cyclohexyl | 1 | F | 6 |
| 5 | cyclohexyl | 1 | F | 6 |
| 7 | cyclohexyl | 1 | F | 6 |
| 3 | phenyl | 1 | F | 6 |
| 5 | phenyl | 1 | F | 6 |
| 3 | pyrimidinyl | 1 | F | 6 |
| 5 | pyrimidinyl | 1 | F | 6 |
| 7 | pyrimidinyl | 1 | F | 6 |

Example 3

A mixture of 30 mmol of NaH, 20 mmol of 2,6-difluoro-4-pentylphenol and 20 ml of THF is stirred for 1 hour at 50° C., and 30 mol of (S)-(−)-propylene oxide are added at 35° C. The resultant intermediate (2,6-difluoro-4-pentyl-1-(2-methyl-2-hydroxyethyl)benzene) is reacted analogously to Example 1 with 2,6-difluoro-4-pentylphenol. Customary work-up and chromatography give 1,2-di-(4-pentyl-2,6-difluorophenyl)oxypropane.

The following are prepared analogously:

$C_nH_{2n+1}$—(A)$_o$—[2,6-difluorophenyl]—O—CH$_2$—CH(CH$_3$)—O—[phenyl with L$^1$, L$^2$]—$C_mH_{2m+1}$

| n | o | A | L$^1$ | L$^2$ | m |
|---|---|---|---|---|---|
| 3 | 0 | — | F | F | 3 |
| 3 | 0 | — | F | F | 5 |
| 5 | 0 | — | F | F | 3 |
| 3 | 1 | H (cyclohexyl) | H | H | 3 |
| 5 | 1 | H (cyclohexyl) | H | H | 5 |
| 7 | 1 | H (cyclohexyl) | F | H | 3 |
| 3 | 1 | H (cyclohexyl) | F | F | 3 |

Example 4

Various liquid-crystalline base materials (A, B) are in each case doped with 1% of 4-[(trans-4-(trans-4-propylcyclohexyl)cyclohexyl]-1-(1-methylheptyloxy)-2,6-difluorobenzene (CCP-308*.F.F). The base mixtures have the following properties and compositions:

| A | | B | |
|---|---|---|---|
| PCH-5F | 10.0 | PCH-5F | 5.0 |
| PCH-6F | 8.0 | PCH-7F | 5.0 |
| PCH-7F | 6.0 | CCP-20CF$_3$ | 8.0 |
| CCP-20CF$_3$ | 8.0 | CCP-30CF$_3$ | 9.0 |
| CCP-30CF$_3$ | 12.0 | CCP-50CF$_3$ | 9.0 |
| CCP-40CF$_3$ | 7.0 | ECCP-3F.F | 11.0 |
| CCP-50CF$_3$ | 11.0 | ECCP-5F.F | 10.0 |
| BCH-3F.F | 12.0 | CUP-3F.F | 5.0 |
| BCH-5F.F | 10.0 | CUP-5F.F | 4.0 |
| ECCP-30CF$_3$ | 5.0 | CCP-30CF$_2$.F.F. | 8.0 |
| ECCP-50CF$_3$ | 5.0 | CCP-50CF$_2$.F.F. | 14.0 |
| CBC-33F | 2.0 | CP-30CF$_3$ | 6.0 |
| CBC-52F | 2.0 | CP-50CF$_3$ | 6.0 |
| CBC-55F | 2.0 | | |

| Physical data | A | B |
|---|---|---|
| S → N (°C.): | <−40 | <−40 |
| Clearing point (°C.): | +92 | +103 |
| Viscosity (mm$^2$s$^{-1}$) at 20° C. | 15 | 21 |
| Δn | 0.0969 | 0.0848 |
| Δε | +5.2 | +6.9 |

The helical pitch and the holding ratio of the resultant doped mixtures are measured, and the HTP is calculated therefrom. The mixture is subsequently treated with aluminum oxide for 20 minutes, and the helical pitch and holding ratio are re-measured. The values obtained in this way can be used to calculate the residual concentration of the dope after aluminum oxide treatment.

The values obtained are shown in Table I below:

TABLE I

| Measurement | Pitch (μm) | HTP (1/μm) | Dope conc. (%) | HR (20° C.) | HR 100 (°C.) |
|---|---|---|---|---|---|
| A + 1% CCP-308*.F.F | −9.8 | −10.2 | 1.00 | 98.0 | 97.0 |
| A + 1% CCP-308*.F.F + treated | −10.1 | | 0.96 | 98.0 | 96.5 |
| B + 1% CCP-308*.F.F | −9.3 | −10.6 | 1.00 | 97.5 | 80.5 |
| B + 1% CCP-308*.F.F + treated | −9.4 | | 0.99 | 97.5 | 82.3 |

Comparative Example 1

The investigations carried out in Example 4 are carried out using the commercially available dope S-811 (E. Merck, Darmstadt, Germany, 1-methylheptyl 4-(p-hexyloxybenzoyloxy)benzoate). The results obtained are shown in Table II.

TABLE II

| Measurement | Pitch (μm) | HTP (1/μm) | Dope conc. (%) | HR (20° C.) | HR 100 (°C.) |
|---|---|---|---|---|---|
| A + 1% S-811 | −8.8 | −11.3 | 1.00 | 98.0 | 96.0 |
| A + 1% S-811 + treated | −10.8 | | 0.81 | 98.0 | 96.0 |
| B + 1% S-811 | −8.2 | −12.2 | 0.99 | 97.5 | 81.0 |
| B + 1% S-811 + treated | −10.0 | | 0.81 | 97.5 | 78.5 |

A comparison of Table I and Table II makes it clear that the known dope S-811 gives mixtures having lower HR values and is decreased more in concentration by treatment with aluminum oxide than is the novel dope CCP-308*.F.F.

Example 5

A smectic base mixture (BM) comprising

| PYP-706 | 3.3% |
| PYP-707 | 3.3% |
| PYP-708 | 3.3% |
| PYP-709 | 3.3% |
| PYP-906 | 7.8% |
| PYP-909 | 25.6% |
| NCB-804 | 31.1% |
| NCB-76 | 15.6% |
| BCN-55 | 6.7% | is doped in each case with 10% of the novel dope of the formula IA.

The properties of the resultant ferroelectric media are shown in Table III:

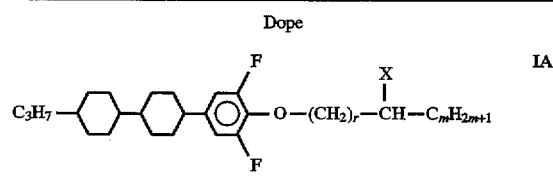

| | | | |
|---|---|---|---|
| IA 1: | r = 0 | X = CH$_3$ | m = 3 |
| IA 2: | r = 0 | X = CH$_3$ | m = 6 |
| IA 3: | r = 1 | X = F | m = 6 |

TABLE III

| Dope | Phase transitions [in C cm$^2$] |
|---|---|
| IA 1 | C < 0 S$_c$* 54 S$_A$ 90 Ch 120.0 I |
| IA 2 | C < 0 S$_c$* 52 S$_A$ 88 Ch 98.0 I |
| IA 3 | C < 0 S$_c$* 51 S$_A$ 91 Ch 103.0 I |

Example 6

12 mmol of 24% sodium hydroxide solution are added dropwise at 60° C. to a mixture of 10 mmol of 4"-octyl-2,5-difluoro-4-hydroxy-p-terphenyl, 50 mmol of R-(−)-epichlorohydrin, 5 ml of dimethylformamide and 20 mg of benzyltriethylammonium chloride.

The mixture is stirred for one hour and subjected to customary work-up, and 6 mmol of dimethyl propylmalonate, 3.3 mmol of potassium tert-butoxide and 10 ml of tert-butanol are added to 3 mmol of the unpurified epoxide obtained, and the mixture is boiled for 12 hours. Acidification, customary work-up and purification by column chromatography give the optically active butyrolactone of the formula

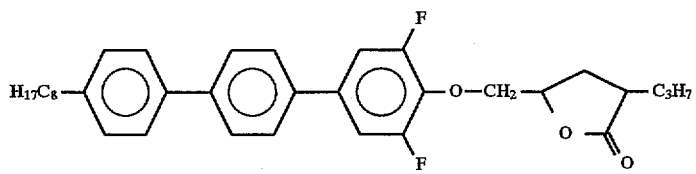

Example 7

A liquid-crystalline base material (C) comprising

| | |
|---|---|
| PCH-5F | 5.0% |
| BCH-2F.F | 5.0% |
| CCP-5OCF3 | 5.0% |
| CUP-2F.F | 6.0% |
| CUP-3F.F | 7.0% |
| CUP-5F.F | 7.0% |
| CCP-2OCF2.F.F | 25.0% |
| CCP-3OCF2.F.F | 20.0% |
| CCP-5OCF2.F.F | 20.0% | is doped with 3% of CCP-308*.F.F. The resultant mixture has the following properties:

| | |
|---|---|
| S → N (°C.): | <−40 |
| Clearing point (°C.): | +75 |
| Viscosity (mm²s⁻¹) at 20° C.: | 34 |
| Δn: | 0.0909 |
| Threshold voltage (V): | 1.28 |

What is claimed is:

1. A chiral compound of formula I1

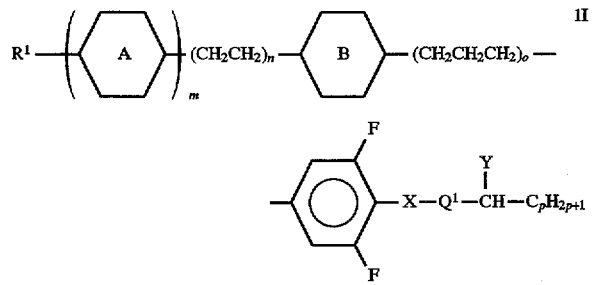

in which

R¹ is F, Cl, CF₃, OCF₃, OCF₂H, CN, alkyl or alkenyl, said alkyl and alkenyl each having 1 to 18 carbon atoms, and are unsubstituted or at least monosubstituted by halogen or monosubstituted by cyano and in which, in addition, one or two non-adjacent CH₂ groups can be replaced by —O— or —S—;

X is O or CH₂;

Q¹ is a C₁₋₈-alkylene group in which, in addition, one or two CH₂ groups can be replaced by —O— or —S— and that two hetero atoms are not adjacent;

Y is CH₃, halogen, CF₃, CF₂H, CH₂F or CN;

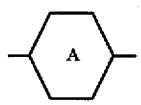

is in each case

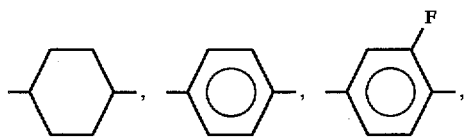

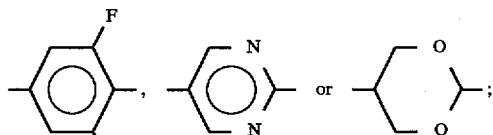

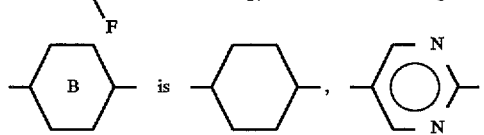

m is 0, 1, or 2;

n and o are each, independently, 0 or 1, and p is from 2 to 8.

2. In a liquid-crystalline medium containing at least two liquid-crystalline components, the improvement wherein said medium contains at least one chiral liquid crystal compound according to claim 1.

3. In an electrooptical display containing a liquid-crystalline medium, the improvement wherein said medium is one of claim 2.

4. A chiral 2,6-difluorobenzene compound of formula I

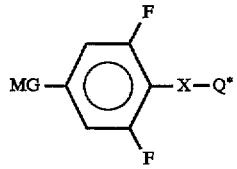

wherein

MG is a mesogenic group of the formula II

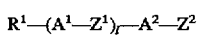

in which

R¹ is F, Cl, CF₃, OCF₃, OCF₂H, CN, alkyl or alkenyl, said alkyl and alkenyl each having 1 to 18 carbon atoms, and are unsubstituted or at least monosubstituted by halogen or monosubstituted by cyano and in which, in addition, one or two non-adjacent $CH_2$ groups can be replaced by —O— or —S—, $A^1$ and $A^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two $CH_2$ groups can each be replaced by O or S, or are thiadiazole-2,5-diyl or 1,4-bicyclo[2.2.2]octylene, wherein at least one $A^1$ group or $A^2$ is
unsubstituted 1,4-cyclohexylene,
unsubstituted 1,4-cyclohexylene in which one or two $CH_2$ groups is in each case replaced by O or S,
1,4-cyclohexylene substituted by one cyano group,
1,4-cyclohexylene substituted by one cyano group and in which one or two $CH_2$ groups is in each case replaced by O or S,
thiadiazol-2,5-diyl,
1,4-bicyclo[2.2.2]octylene,

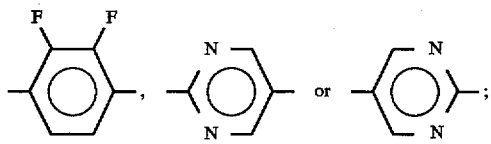

$Z^1$ and $Z^2$ are each, independently, —$OCH_2$—, —$CH_2O$—, —$CH_2CH_2$—, —C≡C— or a single bond, and l is 0, 1, 2 or 3;

X is O or $CH_2$; and

Q* is a chiral radical and is
(a) of formula IIIa

     IIIa wherein m is 0–8 and n is 2–14;
(b) of formula IIIb

     IIIb wherein m is 0–8 and n is 2–14, with the proviso that X is not O;
(c) of formula IIIc

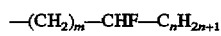     IIIc wherein m is 0–8 and n is 2–14;
(d) of formula IIId

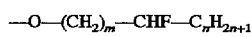     IIId wherein m is 0–8 and n is 2–14, with the proviso that X is not O;
(e) of formula IIIe

     IIIe wherein m is 0–8 and n is 2–14;
(f) of formula IIIf

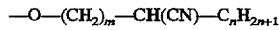     IIIf wherein m is 0–8 and n is 2–14, with the proviso that X is not O;

(g) of formula IVa

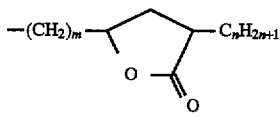     IVa wherein m is 0–8 and n is 2–14;
(h) of formula IVb

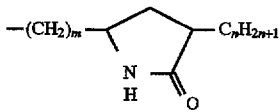     IVb wherein m is 0–8 and n is 2–14;
(i) of formula V

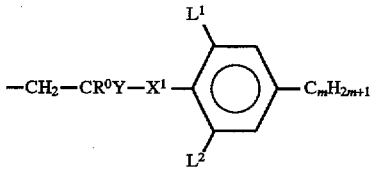     V in which $R^0$ is H or $C_{1-6}$-alkyl which is different from Y,
Y is $CH_3$, halogen, $CF_3$, $CF_2H$, $CH_2F$ or CN,
$X^1$ is —O—, —$CH_2$— or a single bond,
m is 3–5, and
$L^1$ and $L^2$ are each H or F;
(j) of the formula VI

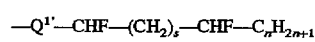     VI wherein
s is 0–6,
n is 1–10, and
$Q^{1'}$ is a $C_{1-8}$-alkylene group in which, in addition, one or two $CH_2$ groups can be replaced by —O— or —S—, and wherein two hetero atoms are not adjacent; or
(k) is of formula VII

     VII wherein
s is 0–6,
n is 1–10, and
$Q^{1'}$ is a $C_{1-8}$-alkylene group in which, in addition, one or two $CH_2$ groups can be replaced by —O— or —S—, and wherein two hetero atoms are not adjacent.

5. In a liquid-crystalline medium containing at least two liquid-crystalline components, the improvement wherein said medium contains at least one chiral liquid crystal compound according to claim 4.

6. In an electrooptical display containing a liquid-crystalline medium the improvement wherein said medium is one of claim 5.

7. A compound according to claim 4, wherein said compound is of formulae Ia, Ib, Ic, Id or Ie

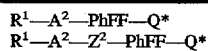

| $R^1$—$A^2$—PhFF—Q* | Ia |
| $R^1$—$A^2$—$Z^2$—PhFF—Q* | Ib |

-continued

| | |
|---|---|
| R¹—A¹—A²—PhFF—Q* | Ic |
| R¹—A¹—A²—Z²—PhFF—Q* | Id |
| R¹—A¹—Z¹—A²—PhFF—Q* | Ie | wherein PhFF is 2,6-difluoro-1,4-phenylene and R¹, A¹, A², Z¹, Z² and Q* are as defined.

8. A compound according to claim 4, wherein A¹ is in each case a substructure of formulae 1–8

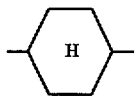 1

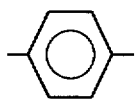 2

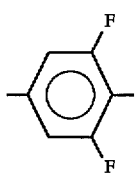 3

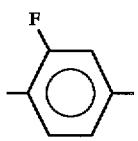 4

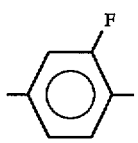 5

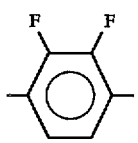 6

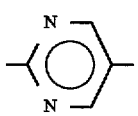 7 or

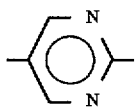 8

9. A compound according to claim 4, wherein Q* is
(a) of formula IIIa

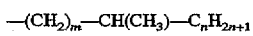   IIIa wherein m is 0–8 and n is 2–14;
(b) of formula IIIb

   IIIb wherein m is 0–8 and n is 2–14, with the proviso that X is not O;
(c) of formula IIIc

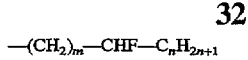   IIIc wherein m is 0–8 and n is 2–14;
(d) of formula IIId

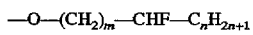   IIId wherein m is 0–8 and n is 2–14, with the proviso that X is not O;
(e) of formula IIIe

   IIIe wherein m is 0–8 and n is 2–14; or
(f) of formula IIIf

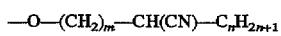   IIIf wherein m is 0–8 and n is 2–14, with the proviso that X is not O.

10. A compound according to claim 4, wherein Q* is of the formula IVa or IVb

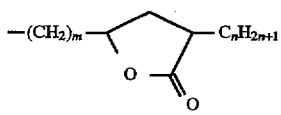   IVa

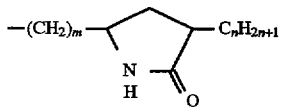   IVb wherein m is 0–8 and n is 2–14.

11. A compound according to claim 4, wherein Q* is of the formula VI or VII

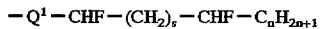   VI

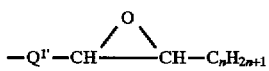   VII wherein
$Q^{1'}$ is a $C_{1-8}$-alkylene group in which, in addition, one or two $CH_2$ groups can be replaced by —O— or —S— and that two hetero atoms are not adjacent;
s is 0–6; and
n is 1–10.

12. A compound of claim 4, wherein X is $CH_2$ and Q* is
(a) of formula IIIa

   IIIa wherein m is 0–8 and n is 2–14;
(b) of formula IIIb

   IIIb wherein m is 0–8 and n is 2–14;
(c) of formula IIIc

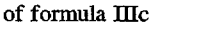   IIIc wherein m is 0–8 and n is 2–14;
(d) of formula IIId

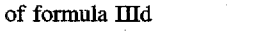   IIId wherein m is 0–8 and n is 2–14;
(e) of formula IIIe

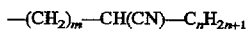      IIIe wherein m is 0–8 and n is 2–14; or
(f) of formula IIIf

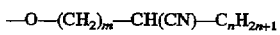      IIIf wherein m is 0–8 and n is 2–14.

13. A liquid-crystalline medium according to claim 5, wherein said liquid-crystalline medium is nematic.

14. In a liquid-crystalline medium containing at least two liquid-crystalline components, the improvement wherein said medium contains at least one chiral liquid crystal compound according to claim 9.

15. In a liquid-crystalline medium containing at least two liquid-crystalline components, the improvement wherein said medium contains at least one chiral liquid crystal compound according to claim 10.

16. In a liquid-crystalline medium containing at least two liquid-crystalline components, the improvement wherein said medium contains at least one chiral liquid crystal compound according to claim 12.

17. In a nematic liquid-crystalline medium containing at least two liquid-crystalline components, the improvement wherein said medium contains at least one chiral 2,6-difluorobenzene compound of formula I

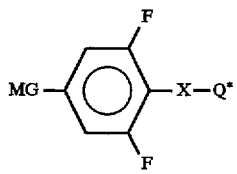      I wherein
MG is a mesogenic group of the formula II

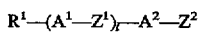      II in which $R^1$ is F, Cl, $CF_3$, $OCF_3$, $OCF_2H$, CN, alkyl or alkenyl, said alkyl and alkenyl each having 1 to 18 carbon atoms, and are unsubstituted or at least mono-substituted by halogen or monosubstituted by cyano and in which, in addition, one or two non-adjacent $CH_2$ groups can be replaced by —O— or —S—, $A^1$ and $A^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two $CH_2$ groups can be replaced by O or S, or are thiadiazole-2,5-diyl or 1,4-bicyclo[2.2.2]octylene, $Z^1$ and $Z^2$ are each, independently, —$OCH_2$—, —$CH_2O$—, —$CH_2CH_2$—, —C≡C— or a single bond, and l is 0, 1, 2 or 3;

X is O or $CH_2$; and

Q* is a chiral radical and is
(a) of formula IIIa

      IIIa wherein m is 0–8 and n is 2–14;
(b) of formula IIIb

      IIIb wherein m is 0–8 and n is 2–14, with the proviso that X is not O;
(c) of formula IIIc

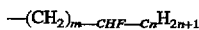      IIIc wherein m is 0–8 and n is 2–14;
(d) of formula IIId

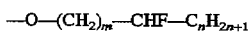      IIId wherein m is 0–8 and n is 2–14, with the proviso that X is not O;
(e) of formula IIIe

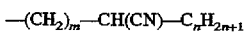      IIIe wherein m is 0–8 and n is 2–14;
(f) of formula IIIf

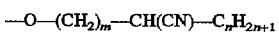      IIIf wherein m is 0–8 and n is 2–14, with the proviso that X is not O;
(g) of formula IVa

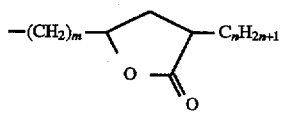      IVa wherein m is 0–8 and n is 2–14;
(h) of formula IVb

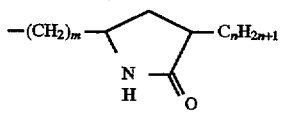      IVb wherein m is 0–8 and n is 2–14;
(i) of formula V

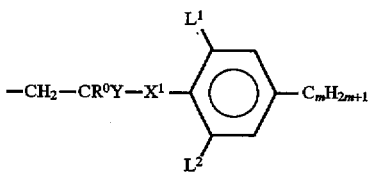      V in which $R^0$ is H or $C_{1-6}$-alkyl which is different from Y, Y is $CH_3$, halogen, $CF_3$, $CF_2H$, $CH_2F$ or CN, X' is —O—, —$CH_2$— or a single bond, m is 3–5, and $L^1$ and $L^2$ are each H or F;
(i) of the formula VI

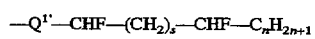      VI wherein s is 0–6, n is 1–10, and $Q^{1'}$ is a $C_{1-8}$-alkylene group in which, in addition, one or two $CH_2$ groups can be replaced by —O— or —S—, and wherein two hetero atoms are not adjacent; or (k) is of formula VII

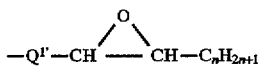

wherein s is 0–6, n is 1–10, and $Q^{1'}$ is a $C_{1-8}$-alkylene group in which, in addition, one or two $CH_2$ groups can be replaced by —O— or —S—, and wherein two hetero atoms are not adjacent.

18. A medium compound according to claim 17, wherein $Q^*$ is (a) of formula III

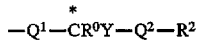

in which $Q^1$ and $Q^2$ are each, independently, a $C_{1-8}$-alkylene group in which, in addition, one or two $CH_2$ groups can be replaced by —O— or —S— and that two hetero atoms are not adjacent, $Q^1$ can also be a single bond, $R^0$ is H or $C_{1-6}$-alkyl which is different from Y, Y is $CH_3$, halogen, $CF_3$, $CF_2H$, $CH_2F$ or CN, $R^2$ is $C_{1-6}$-alkyl, and € is a chiral carbon atom having four different substituents, with the proviso that $R^0$, Y and —$Q^2$—$R^2$ are different from one another; or (b) of formula IV

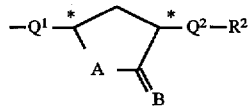

in which $Q^1$ and $Q^2$ are each, independently, a $C_{1-8}$-alkylene group in which, in addition, one or two $CH_2$ groups can be replaced by —O— or —S— and that two hetero atoms are not adjacent, $Q^1$ can also be a single bond, $R^2$ is $C_{1-6}$-alkyl, A is O, S or NH, and B is $H_2$, $CH_2$, O or S.

19. A medium according to claim 18, wherein $Q^*$ is of formula III

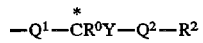

in which $Q^1$ and $Q^2$ are each, independently, a $C_{1-8}$-alkylene group in which, in addition, one or two $CH_2$ groups can be replaced by —O— or —S— and that two hetero atoms are not adjacent, $Q^1$ can also be a single bond, $R^0$ is H or $C_{1-6}$-alkyl which is different from Y, Y is $CH_3$, halogen, $CF_3$, $CF_2H$, $CH_2F$ or CN, $R^2$ is $C_{1-6}$-alkyl, and € is a chiral carbon atom having four different substituents, with the proviso that $R^0$, Y and —$Q^2$—$R^2$ are different from one another.

20. In an electrooptical display containing a liquid-crystalline medium, the improvement wherein said medium is one of claim 17.

21. A medium according to claim 17, wherein $Q^*$ is (a) of formula IIIa

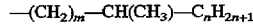

wherein m is 0–8 and n is 2–14;

(b) of formula IIIb

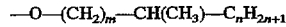

wherein m is 0–8 and n is 2–14, with the proviso that X is not O;

(c) of formula IIIc

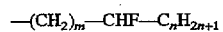

wherein m is 0–8 and n is 2–14;

(d) of formula IIId

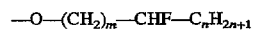

wherein m is 0–8 and n is 2–14, with the proviso that X is not O;

(e) of formula IIIe

wherein m is 0–8 and n is 2–14; or (f) of formula IIIf

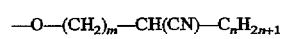

wherein m is 0–8 and n is 2–14, with the proviso that X is not O.

22. A medium according to claim 17, wherein $Q^*$ is of the formula IVa or IVb

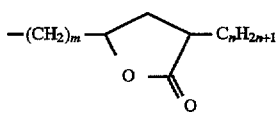

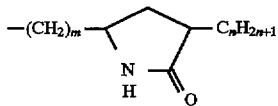

wherein m is 0–8 and n is 2–14.

23. A medium of claim 17, wherein X is $CH_2$ and $Q^*$ is (a) of formula IIIa

wherein m is 0–8 and n is 2–14;

(b) of formula IIIb

wherein m is 0–8 and n is 2–14;

(c) of formula IIIc

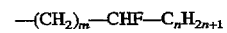

wherein m is 0–8 and n is 2–14;

(d) of formula IIId

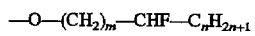   IIId wherein m is 0–8 and n is 2–14;

(e) of formula IIIe

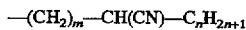   IIIe wherein m is 0–8 and n is 2–14; or (f) of formula IIIf

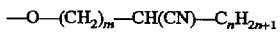   IIIf wherein m is 0–8 and n is 2–14.

24. In a nematic liquid-crystalline medium comprising a nematic base mixture of liquid crystal compounds and a chiral dopant, the improvement wherein said chiral dopant is resistant to decreases in concentration resulting from treatment of said medium with an adsorbent.

25. A nematic medium according to claim 24, wherein said dopant contains no ester groups.

26. A nematic medium according to claim 24, wherein said chiral dopant is a compound of the formula I

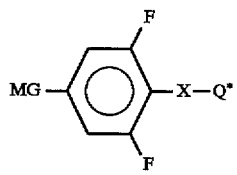   I wherein

MG is a mesogenic group of the formula II $R^1-(A^1-Z^1)_l-A^2-Z^2$   II in which $R^1$ is F, Cl, $CF_3$, $OCF_3$, $OCF_2H$, CN, alkyl or alkenyl, said alkyl and alkenyl each having 1 to 18 carbon atoms, and are unsubstituted or at least monosubstituted by halogen or monosubstituted by cyano and in which, in addition, one or two non-adjacent $CH_2$ groups can be replaced by —O— or —S—, $A^1$ and $A^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two $CH_2$ groups can each be replaced by O or S, or are thiadiazole-2,5-diyl or 1,4-bicyclo[2.2.2]octylene, wherein at least one $A^1$ group or $A^2$ is
  unsubstituted 1,4-cyclohexylene,
  unsubstituted 1,4-cyclohexylene in which one or two $CH_2$ groups is in each case replaced by O or S,
  1,4-cyclohexylene substituted by one cyano group,
  1,4-cyclohexylene substituted by one cyano group and in which one or two $CH_2$ groups is in each case replaced by O or S,
  thiadiazol-2,5-diyl, 1,4-bicyclo[2.2.2]octylene,

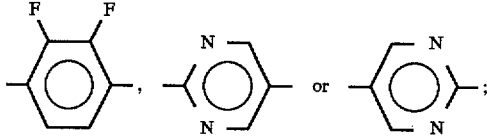

$Z^1$ and $Z^2$ are each, independently, —$OCH_2$—, —$CH_2O$—, —$CH_2CH_2$—, —C≡C— or a single bond, and l is 0, 1, 2 or 3;

X is O or $CH_2$; and

Q* is a chiral radical and is (a) of formula IIIa

   IIIa wherein m is 0–8 and n is 2–14;

(b) of formula IIIb

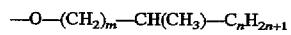   IIIb wherein m is 0–8 and n is 2–14, with the proviso that X is not O;

(c) of formula IIIc

   IIIc wherein m is 0–8 and n is 2–14;

(d) of formula IIId

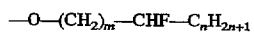   IIId wherein m is 0–8 and n is 2–14, with the proviso that X is not O;

(e) of formula IIIe

   IIIe wherein m is 0–8 and n is 2–14;

(f) of formula IIIf

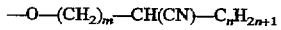   IIIf wherein m is 0–8 and n is 2–14, with the proviso that X is not O;

(g) of formula IVa

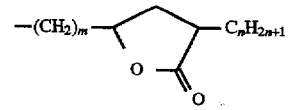   IVa wherein m is 0–8 and n is 2–14;

(h) of formula IVb

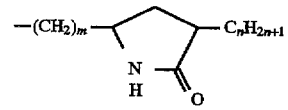   IVb wherein m is 0–8 and n is 2–14;

(i) of formula V

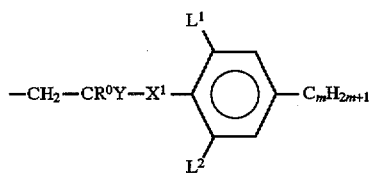

in which
$R^0$ is H or $C_{1-6}$-alkyl which is different from Y,
Y is $CH_3$, halogen, $CF_3$, $CF_2H$, $CH_2F$ or CN,
X' is —O—, —$CH_2$— or a single bond,
m is 3–5, and
$L^1$ and $L^2$ are each H or F;

(j) of the formula VI

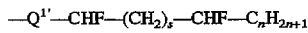

wherein
s is 0–6,
n is 1–10, and
$Q^{1'}$ is a $C_{1-8}$-alkylene group in which, in addition, one or two $CH_2$ groups can be replaced by —O— or —S—, and wherein two hetero atoms are not adjacent; or (k) is of formula VII

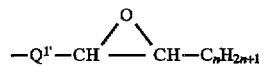

wherein
s is 0–6,
n is 1–10, and
$Q^{1'}$ is a $C_{1-8}$-alkylene group in which, in addition, one or two $CH_2$ groups can be replaced by —O— or —S—, and wherein two hetero atoms are not adjacent.

27. A nematic medium according to claim 24, wherein said adsorbent is aluminum oxide.

28. A nematic medium according to claim 24, wherein one or more of said liquid-crystal compounds is an achiral compound selected azoxybenzenes, benzylidene anilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexylpyridazines and their N oxides, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

29. A nematic medium according to claim 26, wherein Q* is (a) of formula IIIa

   IIIa wherein m is 0–8 and n is 2–14;

(b) of formula IIIb

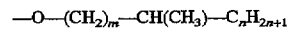   IIIb wherein m is 0–8 and n is 2–14, with the proviso that X is not O;

(c) of formula IIIc

   IIIc wherein m is 0–8 and n is 2–14;

(d) of formula IIId

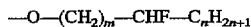   IIId wherein m is 0–8 and n is 2–14, with the proviso that X is not O;

(e) of formula IIIe

   IIIe wherein m is 0–8 and n is 2–14; or (f) of formula IIIf

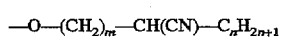   IIIf wherein m is 0–8 and n is 2–14, with the proviso that X is not O.

30. A nematic medium according to claim 26, wherein Q* is of the formula IVa or IVb

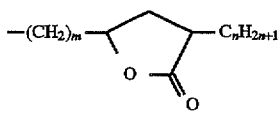   IVa

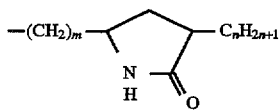   IVb wherein m is 0–8 and n is 2–14.

31. A nematic medium of claim 26, wherein X is $CH_2$ and Q* is (a) of formula IIIa

   IIIa wherein m is 0–8 and n is 2–14;

(b) of formula IIIb

   IIIb wherein m is 0–8 and n is 2–14;

(c) of formula IIIc

   IIIc wherein m is 0–8 and n is 2–14;

(d) of formula IIId

   IIId wherein m is 0–8 and n is 2–14;

(e) of formula IIIe

   IIIe wherein m is 0–8 and n is 2–14; or (f) of formula IIIf

   IIIf wherein m is 0–8 and n is 2–14.

32. A medium according to claim 24, wherein treatment of said medium with said adsorbent decreases the concentration of said chiral dopant by less than 19%.

33. A medium according to claim 24, wherein treatment of said medium with said adsorbent decreases the concentration of said chiral dopant by 4% or less.

34. A medium according to claim 32, wherein said adsorbent is aluminum oxide.

35. A nematic medium according to claim 34, wherein said chiral dopant contains no ester groups.

36. A nematic medium according to claim 35, wherein said dopant is a compound of formula I

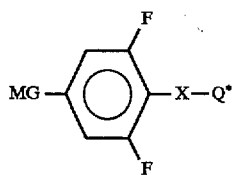   I wherein

MG is a mesogenic group of the formula II

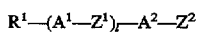   II in which is F, Cl, CF$_3$, OCF$_3$, OCF$_2$H, CN, alkyl or alkenyl, said alkyl and alkenyl each having 1 to 18 carbon atoms, and are unsubstituted or at least mono-substituted by halogen or monosubstituted by cyano and in which, in addition, one or two non-adjacent CH$_2$ groups can be replaced by —O— or —S—, A$^1$ and A$^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two CH$_2$ groups can be replaced by O or S, or are thiadiazole-2,5-diyl or 1,4-bicyclo[2.2.2]octylene, Z$^1$ and Z$^2$ are each, independently, —OCH$_2$—, —CH$_2$O—, —CH$_2$CH$_2$—, —C≡C— or a single bond, and l is 0, 1, 2 or 3;

X is O or CH$_2$; and

Q* is a chiral radical of the formula III

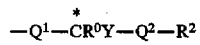   III in which

Q$^1$ and Q$^2$ are each, independently, a C$_{1-8}$-alkylene group in which, in addition, one or two CH$_2$ groups can be replaced by —O— or —S— and that two hetero atoms are not adjacent, Q$^1$ can also be a single bond, R$^0$ is H or C$_{1-6}$-alkyl which is different from Y, Y is CH$_3$, halogen, CF$_3$, CF$_2$H, CH$_2$F or CN, R$^2$ is C$_{1-6}$-alkyl, and € is a chiral carbon atom having four different substituents, with the proviso that R$^0$, Y and —Q$^2$—R$^2$ are different from one another.

37. A nematic medium according to claim 34, wherein said liquid crystal compounds are of formula I

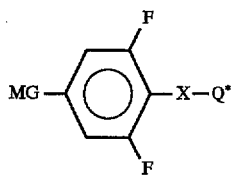   I wherein

MG is a mesogenic group of the formula II

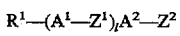   II in which

R$^1$ is F, Cl, CF$_3$, OCF$_3$, OCF$_2$H, CN, alkyl or alkenyl, said alkyl and alkenyl each having 1 to 18 carbon atoms, and are unsubstituted or at least monosubstituted by halogen or monosubstituted by cyano and in which, in addition, one or two non-adjacent CH$_2$ groups can be replaced by —O— or —S—, A$^1$ and A$^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two CH$_2$ groups can be replaced by O or S, or are thiadiazole-2,5-diyl or 1,4-bicyclo[2.2.2]octylene, Z$^1$ and Z$^2$ are each, independently, —OCH$_2$—, —CH$_2$O—, —CH$_2$CH$_2$—, —C≡C— or a single bond, and l is 0, 1, 2 or 3;

X is O or CH$_2$; and

Q* is a chiral radical and is (a) of formula III

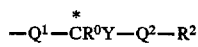   III in which

Q$^1$ and Q$^2$ are each, independently, a C$_{1-8}$-alkylene group in which, in addition, one or two CH$_2$ groups can be replaced by —O— or —S— and that two hetero atoms are not adjacent, Q$^1$ can also be a single bond, R$^0$ is H or C$_{1-6}$-alkyl which is different from Y, Y is CH$_3$, halogen, CF$_3$, CF$_2$H, CH$_2$F or CN, R$^2$ is C$_{1-6}$alkyl, and € is a chiral carbon atom having four different substituents, with the proviso that R$^0$, Y and —Q$^2$—R$^2$ are different from one another;

(b) of formula IV

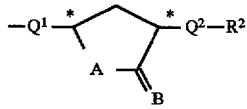   IV in which

Q$^1$ and Q$^2$ are each, independently, a C$_{1-8}$-alkylene group in which, in addition, one or two CH$_2$ groups can be replaced by —O— or —S— and that two hetero atoms are not adjacent, Q$^1$ can also be a single bond, R$^2$ is C$_{1-6}$-alkyl, A is O, S or NH, and B is H$_2$, CH$_2$, O or S;

(c) of formula V

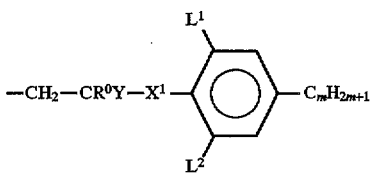

in which
  $R^0$ is H or $C_{1-6}$-alkyl which is different from Y,
  Y is $CH_3$, halogen, $CF_3$, $CF_2H$, $CH_2F$ or CN,
  X' is —O—, —$CH_2$— or a single bond,
  m is 3–5, and
  $L^1$ $L^2$ are each H or F;
(d) of the formula VI

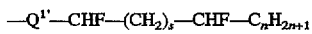

wherein
  s is 0–6,
  n is 1–10, and
  $Q^{1'}$ is a $C_{1-8}$-alkylene group in which, in addition, one or two $CH_2$ groups can be replaced by —O— or —S— and that two hetero atoms are not adjacent; or
(e) is of formula VII

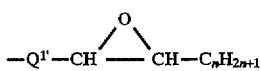

wherein
  s is 0–6,
  n is 1–10, and
  $Q^{1'}$ is a $C_{1-8}$-alkylene group in which, in addition, one or two $CH_2$ groups can be replaced by —O— or —S— and that two hetero atoms are not adjacent.

38. A method of increasing holding ratio of a doped nematic liquid-crystalline mixture subjected to purification by an adsorbent, said method comprising:
  adding a chiral dopant to a nematic mixture of liquid-crystalline compounds wherein said dopant is resistant to decreases in concentration resulting from treatment with an adsorbent; and
  thereafter subjecting the resultant doped nematic mixture to treatment with an adsorbent.

39. A method according to claim 38, wherein said chiral dopant is of formula I

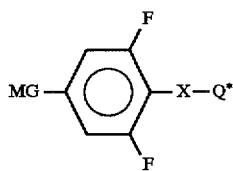

wherein
  MG is a mesogenic group of the formula II

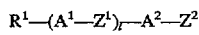

in which
  $R^1$ is F, Cl, $CF_3$, $OCF_3$, $OCF_2H$, CN, alkyl or alkenyl, said alkyl and alkenyl each having 1 to 18 carbon atoms, and are unsubstituted or at least monosubstituted by halogen or monosubstituted by cyano and in which, in addition, one or two non-adjacent $CH_2$ groups can be replaced by —O— or —S—, $A^1$ and $A^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two $CH_2$ groups can each be replaced by O or S, or are thiadiazole-2,5-diyl or 1,4-bicyclo[2.2.2]octylene, $Z^1$ and $Z^2$ are each, independently, —$OCH_2$—, —$CH_2O$—, —$CH_2CH_2$—, —C≡C— or a single bond, and l is 0, 1, 2 or 3;

X is O or $CH_2$; and

Q* is a chiral radical and is
  (a) of formula III

in which
  $Q^1$ and $Q^2$ are each, independently, a $C_{1-8}$-alkylene group in which, in addition, one or two $CH_2$ groups can be replaced by —O— or —S— and that two hetero atoms are not adjacent,
  $Q^1$ can also be a single bond,
  $R^0$ is H or $C_{1-6}$-alkyl which is different from Y,
  Y is $CH_3$, halogen, $CF_3$, $CF_2H$, $CH_2F$ or CN,
  $R^2$ is $C_{1-6}$-alkyl, and
  C* is a chiral carbon atom having four different substituents,
    with the proviso that $R^0$, Y and —$Q^2$—$R^2$ are different from one another;
(b) of formula IV

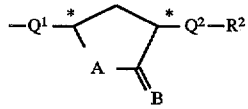

in which
  $Q^1$ and $Q^2$ are each, independently, a $C_{1-8}$-alkylene group in which, in addition, one or two $CH_2$ groups can be replaced by —O— or —S— and that two hetero atoms are not adjacent,
  $Q^1$ can also be a single bond,
  $R^2$ is $C_{1-6}$-alkyl,
  A is O, S or NH, and
  B is $H_2$, $CH_2$, O or S; or
(c) of formula V

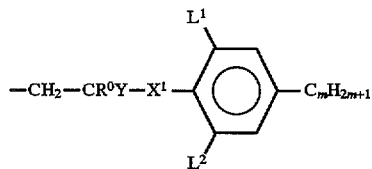

in which
  $R^0$ is H or $C_{1-6}$-alkyl which is different from Y,
  Y is $CH_3$, halogen, $CF_3$, $CF_2H$, $CH_2F$ or CN,
  X' is —O—, —$CH_2$— or a single bond,
  m is 3–5, and
  $L^1$ and $L^2$ are each H or F.

40. A method according to claim 38, wherein, following treatment with said adsorbent, the concentration of said chiral dopant within said nematic mixture is decreased by 4% or less.

41. A method according to claim 38, wherein said adsorbent is aluminum oxide.

42. A method according to claim 38, wherein one or more of said liquid-crystal compounds is an achiral compound selected from azoxybenzenes, benzylidene anilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexylpyridazines and their N oxides, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

43. A method according to claim 39, wherein Q* is
(a) of formula IIIa

$$—(CH_2)_m—CH(CH_3)—C_nH_{2n+1} \qquad \text{IIIa}$$

wherein m is 0–8 and n is 2–14;

(b) of formula IIIb $$—O—(CH_2)_m—CH(CH_3)—C_nH_{2n+1} \qquad \text{IIIb}$$

wherein m is 0–8 and n is 2–14, with the proviso that X is not O;

(c) of formula IIIc $$—(CH_2)_m—CHF—C_nH_{2n+1} \qquad \text{IIIc}$$

wherein m is 0–8 and n is 2–14;

(d) of formula IIId $$—O—(CH_2)_m—CHF—C_nH_{2n+1} \qquad \text{IIId}$$

wherein m is 0–8 and n is 2–14, with the proviso that X is not O;

(e) of formula IIIe $$—(CH_2)_m—CH(CN)—C_nH_{2n+1} \qquad \text{IIIe}$$

wherein m is 0–8 and n is 2–14; or (f) of formula IIIf $$—O—(CH_2)_m—CH(CN)—C_nH_{2n+1} \qquad \text{IIIf}$$

wherein m is 0–8 and n is 2–14, with the proviso that X is not O.

44. A method according to claim 39, wherein Q* is of the formula IVa or IVb

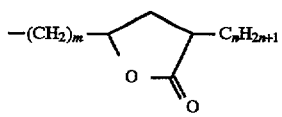

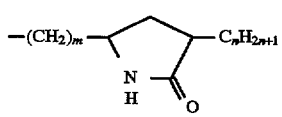

wherein m is 0–8 and n is 2–14.

45. A method according to claim 38, wherein, following treatment with said adsorbent, the concentration of said chiral dopant within said nematic mixture is decreased by less than 19%.

46. A chiral 2,6-difluorobenzene compound of formula I

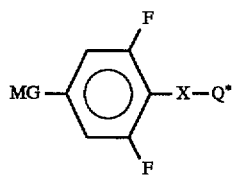

wherein
MG is a mesogenic group of the formula II $$R^1—(A^1—Z^1)_l—A^2—Z^2 \qquad \text{II}$$

in which
R$^1$ is F, Cl, CF$_3$, OCF$_3$, OCF$_2$H, CN, alkyl or alkenyl, said alkyl and alkenyl each having 1 to 18 carbon atoms, and are unsubstituted or at least mono-substituted by halogen or monosubstituted by cyano and in which, in addition, one or two non-adjacent CH$_2$ groups can be replaced by —O— or —S—, A$^1$ and A$^2$ are each, independently of one another, 1,4-phenylene which is unsubstituted or substituted by 1 or 2 fluorine atoms and in which, in addition, one or two CH groups can be replaced by N, or are 1,4-cyclohexylene which is unsubstituted or substituted by one cyano group and in which, in addition, one or two CH$_2$ groups can each be replaced by O or S, or are thiadiazole-2,5-diyl or 1,4-bicyclo[2.2.2] octylene, wherein at least one A$^1$ group or A$^2$ is
unsubstituted 1,4-cyclohexylene,
unsubstituted 1,4-cyclohexylene in which one or two CH$_2$ groups is in each case replaced by O or S,
1,4-cyclohexylene substituted by one cyano group,
1,4-cyclohexylene substituted by one cyano group and in which one or two CH$_2$ groups is in each case replaced by O or S,
thiadiazol-2,5-diyl,
1,4-bicyclo[2.2.2]octylene,

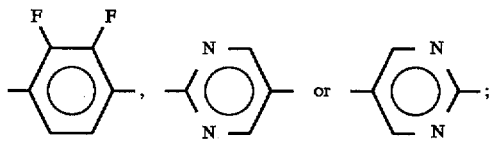

Z$^1$ and Z$^2$ are each, independently, —OCH$_2$—, —CH$_2$O—, —CH$_2$CH$_2$—, —C≡C— or a single bond, and l is 0, 1, 2 or 3;

X is O or CH$_2$; and

Q* is a chiral radical and is
(a) of formula III $$—Q^1—\overset{*}{C}R^0Y—Q^2—R^2 \qquad \text{III}$$

in which
Q$^1$ and Q$^2$ are each, independently, a C$_{1-8}$-alkylene group in which, in addition, one or two CH$_2$ groups can be replaced by —O— or —S— and that two hetero atoms are not adjacent,
Q$^1$ can also be a single bond,
R$^0$ is H or C$_{1-6}$-alkyl which is different from Y, Y is $CH_3$, halogen, $CF_3$, $CF_2H$, $CH_2F$ or CN,
$R^2$ is $C_{1-6}$-alkyl, and
© is a chiral carbon atom having four different substituents, with the proviso that $R^0$, Y and $-Q^2-R^2$ are different from one another;

(b) of formula IV

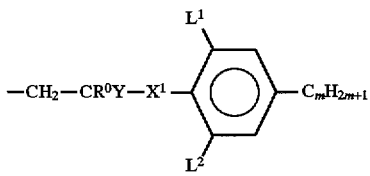   IV in which
$Q^1$ and $Q^2$ are each, independently, a $C_{1-8}$-alkylene group in which, in addition, one or two $CH_2$ groups can be replaced by —O— or —S— and that two hereto atoms are not adjacent,
$Q^1$ can also be a single bond,
$R^2$ is $C_{1-6}$-alkyl,
A is O, S or NH, and
B is $H_2$, $CH_2$, O or S;

(c) of formula V

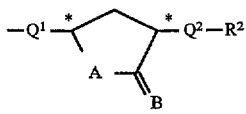 V in which $R^0$ is H or $C_{1-6}$-alkyl which is different from Y,
Y is $CH_3$, halogen, $CF_3$, $CF_2H$, $CH_2F$ or CN,
X' is —O—, —$CH_2$— or a single bond,
m is 3–5, and
$L^1$ and $L^2$ are each H or F;

(d) of the formula VI

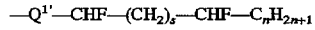 VI wherein
s is 0–6,
n is 1–10, and
$Q^{1'}$ is a $C_{1-8}$-alkylene group in which, in addition, one or two $CH_2$ groups can be replaced by —O— or —S— and that two hetero atoms are not adjacent; or (e) is of formula VII

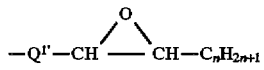 VII wherein
s is 0–6,
n is 1–10, and
$Q^{1'}$ is a $C_{1-8}$-alkylene group in which, in addition, one or two $CH_2$ groups can be replaced by —O— or —S— and that two hetero atoms are not adjacent.

* * * * *